(12) United States Patent
Hepler

(10) Patent No.: US 6,936,273 B2
(45) Date of Patent: Aug. 30, 2005

(54) LIPOSOMAL ANALGESIC FORMULATION AND USE

(75) Inventor: Douglas I. Hepler, McLeansville, NC (US)

(73) Assignee: IDEXX Laboratories, Inc., Westbrook, ME (US)

( * ) Notice: Subject to any disclaimer, the term of this patent is extended or adjusted under 35 U.S.C. 154(b) by 0 days.

(21) Appl. No.: 10/327,575

(22) Filed: Dec. 20, 2002

(65) Prior Publication Data

US 2004/0121987 A1 Jun. 24, 2004

(51) Int. Cl.$^7$ ................................................. A61K 9/127
(52) U.S. Cl. ..................... 424/450; 514/557; 514/561; 514/569; 514/577
(58) Field of Search .................. 424/450; 514/557, 514/561, 569, 577

(56) References Cited

U.S. PATENT DOCUMENTS

| | | | |
|---|---|---|---|
| 3,558,690 A | 1/1971 | Sallman et al. ............. | 260/471 |
| 4,761,288 A | 8/1988 | Mezei ........................ | 424/450 |
| 4,897,269 A | 1/1990 | Mezei ........................ | 424/450 |
| 4,937,078 A | 6/1990 | Mezei et al. ................ | 424/450 |
| 5,154,930 A | 10/1992 | Popescu et al. ............. | 424/489 |
| 5,738,869 A | 4/1998 | Fischer et al. .............. | 424/450 |
| 6,045,827 A * | 4/2000 | Russell ....................... | 424/485 |
| 6,117,455 A | 9/2000 | Takada et al. .............. | 424/501 |
| 6,287,587 B2 | 9/2001 | Shigeyuki et al. .......... | 424/426 |
| 6,423,338 B1 | 7/2002 | Larson et al. ............... | 424/450 |

OTHER PUBLICATIONS

International Search Report dated Jul. 2, 2004 for PCT/US03/40717.

* cited by examiner

Primary Examiner—Gollamudi S. Kishore
(74) Attorney, Agent, or Firm—McDonnell Boehnen Hulbert & Berghoff LLP

(57) ABSTRACT

A liposome formulation containing about 1% diclofenac is an effective topical anti-inflammatory topical treatment for lameness in horses. More particularly it has been discovered that a formulation containing vitamin E, phospholipid and diclofenac salt such as the sodium or potassium salt is a highly effective topical anti-inflammatory formulation that is particularly effective in treating lameness in horses.

10 Claims, No Drawings

LIPOSOMAL ANALGESIC FORMULATION AND USE

FIELD OF THE INVENTION

This invention is in the field of liposomal non-steroidal anti-inflammatory formulations.

BACKGROUND OF THE INVENTION

U.S. Pat. No. 5,154,930 describes extensive background in the use of liposomes in the delivery of pharmaceuticals with diclofenac disclosed as a non-steroidal anti-inflammatory. U.S. Pat. No. 5,738,869 specifically describes a phospholipid transdermal drug delivery system containing α-tocopherol, aliphatic alcohol and diclofenac.

Diclofenac is described in U.S. Pat. No. 3,558,690 and in Merck Index 3071 eleventh Edition. Various diclofenac products are described in Physicians Desk Reference.

U.S. Pat. No. 4,937,078 relates to topical delivery of drugs in liposomes.

U.S. Pat. No. 4,761,288 relates to multilamellar lipid vesicles having a saturated solution and solid form of a drug captured therein.

U.S. Pat. No. 4,897,269 relates to topical administration of drugs using drugs captured in lipid vesicles.

U.S. Pat. No. 6,423,338 B1 describes phospholipids containing microcrystals of drugs.

SUMMARY OF THE INVENTION

It has been discovered that a liposome formulation containing about 1% diclofenac is an effective topical anti-inflammatory treatment for lameness in horses. More particularly it has been discovered that a formulation containing vitamin E, phospholipid and diclofenac salt such as the sodium or potassium salt is a highly effective topical anti-inflammatory formulation that is particularly effective in treating lameness in horses.

The invention includes a composition that comprises about 1% vitamin E acetate, 10% phospholipid, 1% diclofenac, 5% propylene glycol, 6% ethanol and about 77% water. The composition comprises 2–10 micron lipid vesicles or liposomes that contain diclofenac. The composition may also contain small amounts of benzethonium chloride or other preservative.

Formulations having 0.5 to 1.5 percent of Vitamin E ester, 5–15% of phospholipid, 0.7 to 1.3 percent diclofenac, 3 to 7% alkylane glycol, 3 to 9 percent of ($C_1$–$C_6$) alcohol and the remainder water or other minor ingredients (i.e. preservatives, perfumes, colorants and the like) are encompassed by the invention.

The composition of this invention is particularly effective in treating lameness in horses. A three to seven inch ribbon, preferably about a five inch ribbon, of the formulation is generally applied twice daily for 3 to 10 days. This equates to between about 20 mg to 120 mg diclofenac, preferably between about 70 mg to 80 mg, per dose. Other dosages can be used, such as those disclosed in U.S. Pat. No. 4,937,078, the contents of that is incorporated herein by reference.

DETAILED DESCRIPTION OF THE INVENTION

EXAMPLE I

Formulation Preparation

To a 600 gallon jacketed stainless steel kettle equipped with a primary scraper and a secondary mixer is added 396 grams of benzethonium chloride in about 602 grams of purified water at a temperature of 55° to 65° C. The benzethonium chloride container is rinsed with an addition of 602 grams of water. To the solution in the kettle is added 118.8 kg of ethanol and 99.0 kg of propylene glycol.

Mix 19.8 kg of vitamin E acetate, 200.6 kg of phospholipon 90H HYD lecithin, and 19.8 kg of diclofenac sodium is added in sequence to an auxiliary tank at 55° C. to 65° C. and mixed for about 15 minutes. The auxiliary tank is weighed and evaporated alcohol is replaced. The material in the auxiliary tank is passed into the manufacturing kettle at a rate of 3 to 5 kg/minute and the auxiliary tank is rinsed twice with 13.2 kg of water at 55° C. to 65° C. The bulk material in the manufacturing kettle is passed through a 60 mesh screen during circulation. The circulation rate is about 95 kg to 105 kg per minute.

The vessel bulk mixture is stirred and cooled to 30° C. and after cooling for about 45 minutes a sample is removed and tested for temperature and mean volume vesicle particle size. When the temperature is about 32° C. and the liposome vesicle particle size is between 2 and 10 microns agitation is stopped.

Formulations of the invention contain 0.5 to 1.5% of vitamin E or a $C_2$–$C_6$ ester of vitamin E; 5–15% phospholipid; 3 to 7% alkylane glycol containing 2–5 carbon atoms, preferably propylene glycol; 3–9% of ($C_1$–$C_6$) alcohol, perferably ethanol; 0.7 to 1.3 percent diclofenac, perferably about 1%; and the remainder water wherein the formulation contains 2–10 micron lipid vesicles.

The preferred phospholipid is phospholipon 90H HYD Lechthin sold by Rhone-Poulenc. Other useful lipids are obtainable from a number of sources. Natural phosphatide mixtures from egg or soy containing more than 70% phosphatidylcholine are obtained from a number of commercial sources such as Sigma Chemical of St. Louis, Mo., and Lipoid KG, Ludwigshafen, West Ger., Hepar of Franklin, Ohio. Hepar supplies egg phosphatidylcholine. Other sources of lipid such as soy phosphatidylcholine are American Lecithin, Woodside, L.I., N.Y., and Riceland Foods, Little Rock, Ark. Phosphatidic acid of 99% purity is obtained from Avanti Chemical of Birmingham, Ala.

Purified natural soybean lecithin having about 80% phosphotidylcholine 2% lysophosphatidylcholine, 4% phosphatic acid and about 1% monophosphatidylinositol is suitable for practicing the invention. Those skilled in the art will recognize a variety of suitable phospholipid compositions useful in the present invention.

EXAMPLE II

Clinical Study

A clinical study was performed utilizing the 1% of diclofenac formulation described above. Lameness was graded using the AAEP (American Association of Equine Practitioners) scale. Pain, joint mobility and lameness were evaluated. The clinical investigator was completely masked to study treatment. Each tube of test article was identified only by study case number. The study was conducted for five days. During the study, between about 20 to 114 mg diclofenac were applied twice daily. On average, each dose was achieved by applying a five-inch ribbon of suspension (approximately 73 mg diclofenac per dose).

The study was performed on 116 horses in eight states. The test article had a significant positive effect on lameness, pain and owners's evaluation of lameness. There was no significant effect on joint mobility in this study.

| Results | | | |
|---|---|---|---|
| Parameter | Placebo | Diclofenac | Comments |
| Lameness | | | |
| ΔL (S.D.) | −0.02 (1.12) | −1.48 (1.07) | p < 0.0001 |
| Lameness Improved | 17/56 (30%) | 46/60 (77%) | p < 0.0001 |
| Pain | | | |
| ΔP (S.D.) | 0.00 (0.91) | −0.48 (0.68) | p = 0.0025 |
| Pain Improved | 15/56 (27%) | 23/60 (38%) | P = 0.1299 |
| Mobility Improved | 9/56 (16%) | 15/60 (25%) | p = 0.1694 |
| Owner Improved | 21/56 (38%) | 47/59 (80%) | p < 0.0001 |

Of the 60 horses that received the test article, no adverse reactions were attributable to topical administration of diclofenac. In addition, the data shows that the 1% diclofenac liposomal suspension, applied twice daily was effective in improving three of the four study parameters. Statistically, the effect was highly significant.

Pivotal target animal safety studies were conducted with treatment doses of 0.6, 1.7, 2.8 and 5.6 times the effective dose of 73 mg twice daily. There were no toxic reactions observed, based upon physical examination, CBC, serum biochemistry, gastroscopy gross necropsy, and histopathology. These data support the safety of doses above 73 mg twice daily and treatment duration of 10 days.

A preparation containing 2% diclofenac processed in a similar manner did not contain phospholipid vesicles and was not effective.

What is claimed is:

1. A method for treating lameness in horses comprising providing a topical non-steroidal anti-inflammatory formulation consisting essentially of:
   (a) about 1% diclofenac salt,
   (b) about 5% propylene glycol,
   (c) about 6% ethanol,
   (d) about 1% vitamin E acetate,
   (e) about 10% phospholipid, and
wherein vesicles or liposomes comprising diclofenac salt are present in the formulation, and topically administering the formulation to a horse.

2. The method of treating lameness in horses of claim 1, wherein the formulation comprises 2–10 micron vesicles.

3. The method of claim 1, wherein the formulation is administered twice daily.

4. The method of claim 1, wherein between about 20 mg to about 120 mg of diclofenac is applied as a single dose to the horse.

5. The method of claim 4, wherein between about 70 mg to about 80 mg of diclofenac is applied as a single dose to the horse.

6. The method of claim 4, wherein two doses per day are applied to the horse for at least three days.

7. The method of claim 1, wherein the formulation further consists essentially of a preservative.

8. The method of claim 1, wherein the formulation further consists essentially of a perfume.

9. The method of claim 1, wherein the formulation further consists essentially of a colorant.

10. The method of claim 1, wherein the formulation further consists essentially of about 77% water.

* * * * *